United States Patent [19]

Akiyama

[11] Patent Number: 4,900,145
[45] Date of Patent: Feb. 13, 1990

[54] OPHTHALMIC DISEASE DETECTION APPARATUS

[75] Inventor: Koichi Akiyama, Hino, Japan

[73] Assignee: Kowa Company Ltd., Japan

[21] Appl. No.: 180,211

[22] Filed: Apr. 11, 1988

[30] Foreign Application Priority Data

Apr. 9, 1987 [JP] Japan .................................. 62-85806

[51] Int. Cl.⁴ .............................................. A61B 3/10
[52] U.S. Cl. .................................... 351/221; 351/205; 351/214
[58] Field of Search ........................ 351/204, 214, 221; 128/633

[56] References Cited

U.S. PATENT DOCUMENTS 4,213,678  7/1980  Pomerantzeff .................. 351/221 X Primary Examiner—Rodney B. Bovernick
Attorney, Agent, or Firm—Bruce L. Adams; Van C. Wilks

[57] ABSTRACT

An apparatus for detecting ophthalmic diseases such as an inflammation in a patient's eye which includes means for focussing a laser beam at a selected spot in the eye. The light scattered from the eye is photoelectrically detected and converted into an electrical signal which is subsequently used to determine the protein concentration essential to ophthalmic disease detection in the patient's eye. The laser beam is so deflected that it scans an area in the patient's eye except for a plane which is perpendicular to the scanning direction and includes the corneal vertex of the patient's eye.

6 Claims, 5 Drawing Sheets

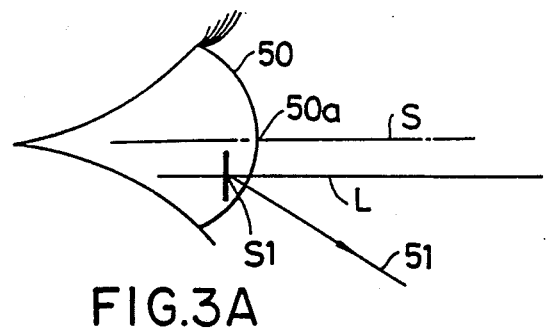
FIG.3A
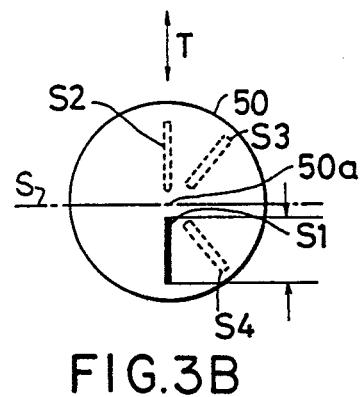
FIG.3B
FIG.4
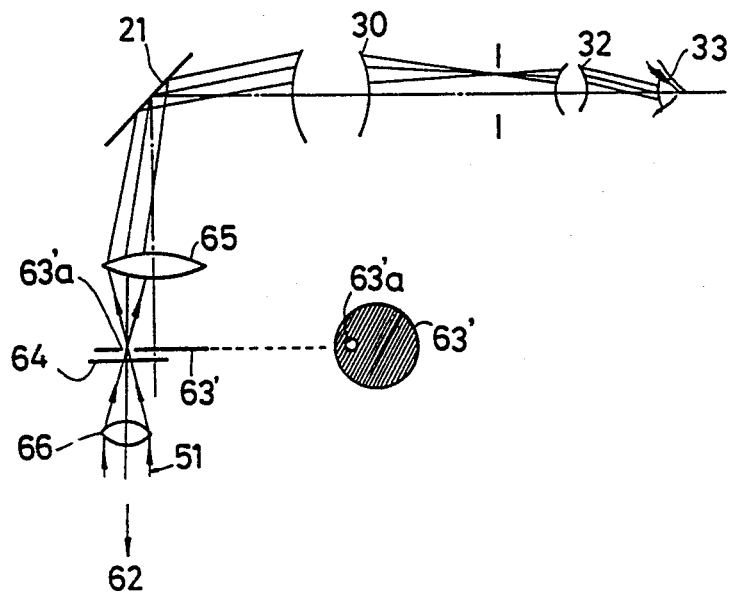

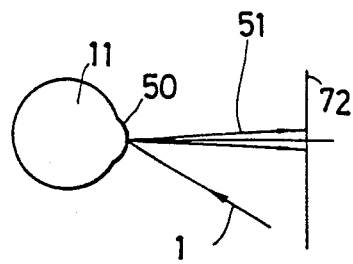 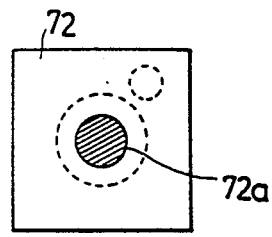
FIG.5A   FIG.5B
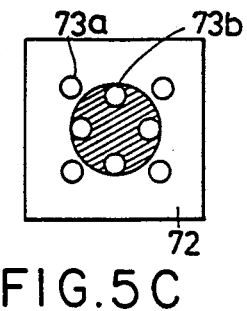 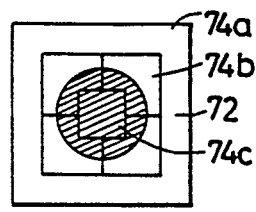
FIG.5C   FIG.5D
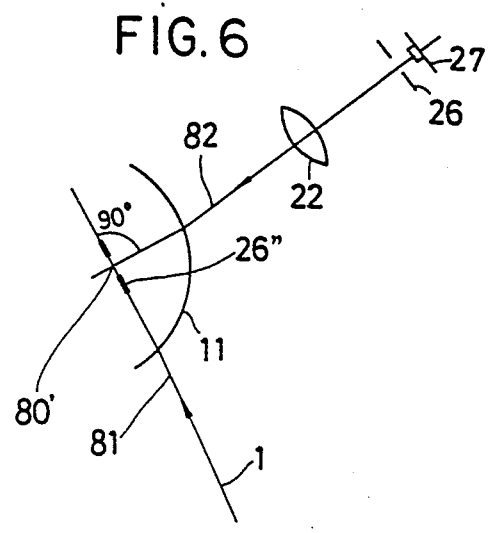
FIG.6

OPHTHALMIC DISEASE DETECTION APPARATUS

BACKGROUND OF THE INVENTION

1. Field of the Invention

This invention relates to an apparatus for detecting ophthalmic diseases in a patient's eye, and more particularly to an apparatus for detecting ophthalmic diseases in which laser light is radiated via an optical system at one spot in the camera oculi of the patient's eye, particularly in the anterior chamber thereof, and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of the ciliary body, iris, and the front surface of the crystalline lens, while the camera oculi posterior is defined by a space surrounded by the rear surface of the iris, inner surface of the ciliary body, and front surface of the crystalline lens. The camera oculi is filled with transparent humor aqueous, which has chemical and physical characteristics different from lymphatic liquid and has a close relation with the metabolism of the cornea or crystalline lens. The humor aqueous contains proteins which increase causing the camera oculi to be turbid when it becomes inflamed.

In this respect, the measurement of protein concentration in the camera oculi of the patient's eye is of great importance in determining whether the camera oculi is inflamed, that is, whether a blood-aqueous barrier functions normally or not.

To measure the protein concentration in the camera oculi, a slit lamp microscope is very often used to determine the turbidity by grading via the naked eyes. This is, however, disadvantageous because the judgment depends upon the person who performs the measurement.

On the other hand, a photographic measuring method has been developed to make a quantitative measurement of the protein concentration. This method is, however, too complicated to analyze, thus very difficult to apply in a clinical examination.

To overcome this problem, an apparatus for detecting the ophthalmic diseases has been proposed which includes means for focussing a laser beam at a selected spot in the camera oculi of an eye. In the apparatus, the light scattered from the eye is photoelectrically detected and converted into an electrical signal which is subsequently used to determine the protein concentration essential to ophthalmic disease detection in the camera oculi of the patient's eye. See, for example, Japanese Patent Laid-open No. 120834/87.

This apparatus, however, has also the drawback that the light reflected or scattered at the cornea, iris, lens or artificial lens after the cataractous operation impinges of the spot to be measured in the anterior chamber or intrudes into the laser scattered light in the form of noises. This disadvantageously makes the measurement inaccurate and the measured value poorly repeatable.

SUMMARY OF THE INVENTION

It is therefore an object of the present invention to provide an apparatus for detecting ophthalmic diseases which is capable of easily and precisely measuring the protein concentration in a patient's eye.

It is another object of the present invention to provide an apparatus for detecting ophthalmic diseases which is capable of reducing or removing noises due to the reflected or scattered light which may impinges on the spot be measured in the patient's eye.

In accordance with the present invention, the ophthalmic disease detection apparatus disclosed herein includes means for focussing a laser beam at a selected spot in a patient's eye. The laser beam is deflected in a predetermined direction to scan an area including the spot to be measured in the patient's eye. The apparatus further includes photoelectric converting means for receiving light scattered from the patient's eye and converting it into an electric signal, and a mask disposed in the front of the photoelectric converting means and formed thereon with a slit having a predetermined width to limit the impinging of the scattered light on the photoelectric converting means. The laser beam is so deflected that it scans an area in the patient's eye except for a plane which is perpendicular to the scanning direction and includes the corneal vertex of the patient's eye.

Generally, when a plane that includes the optical axes of the laser beam projector and the light receiving means does not pass through the corneal vertex, corneal reflex laser light is reflected away from this plane owing to the convexity of the cornea. As this plane is set to form a plane perpendicular to the scanning direction that does not include the corneal vertex, the corneal reflex light is reflected away from the light receiving means, enabling the corneal reflex light, which is a major cause of noise, to be removed from the received light signal, thereby improving the detection precision. Moreover, as the corneal reflex light is quite directional, positional alignment of the patient's eye and the detection apparatus can be readily performed by receiving this reflected light and measuring its intensity and position.

In a preferred embodiment, the area of the patient's eye to be scanned lies under the plane which is perpendicular to the scanning direction and includes the corneal vertex of the patient's eye.

In another preferred embodiment, the size and/or position of corneal reflex light on a surface fixed to the laser beam projector or the light receiving means is/are determined for positional alignment between the patient's eye and the apparatus.

The laser beam projector and light receiving means are preferably arranged so that their optical axis cross substantially at right angles or at an angle other than 90 degrees.

BRIEF DESCRIPTION OF THE DRAWINGS

The objects and features of the present invention will become more apparent from a consideration of the following detailed description taken in conjunction with the accompanying drawings in which:

FIGS. 3(A) and 3(B) are explanatory views relating to laser beam scanning width.

FIG. 4 is a view showing the arrangement of an optical system for observation of corneal reflex light.

FIG. 5(A) is a view of another embodiment of an optical system for observation of corneal reflex light.

FIG. 5(B) to 5(D) are explanatory views showing light-receiving plate embodiments.

FIG. 6 is a view showing the positional arrangement when the optical axes of the laser beam projector and the light receiving means are disposed at about 90 degrees to each other.

DETAILED DESCRIPTION OF THE PREFERRED EMBODIMENTS

Figure 1:
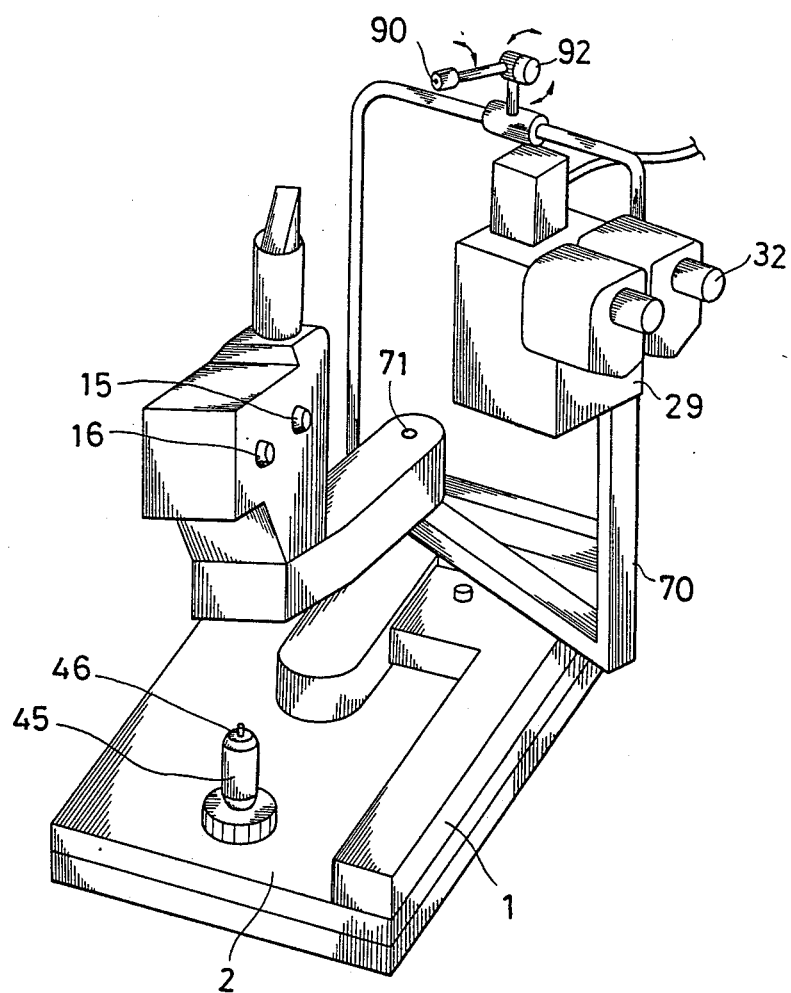
FIG. 1 is a perspective view of the detection apparatus according to the present invention.
Figure 2:
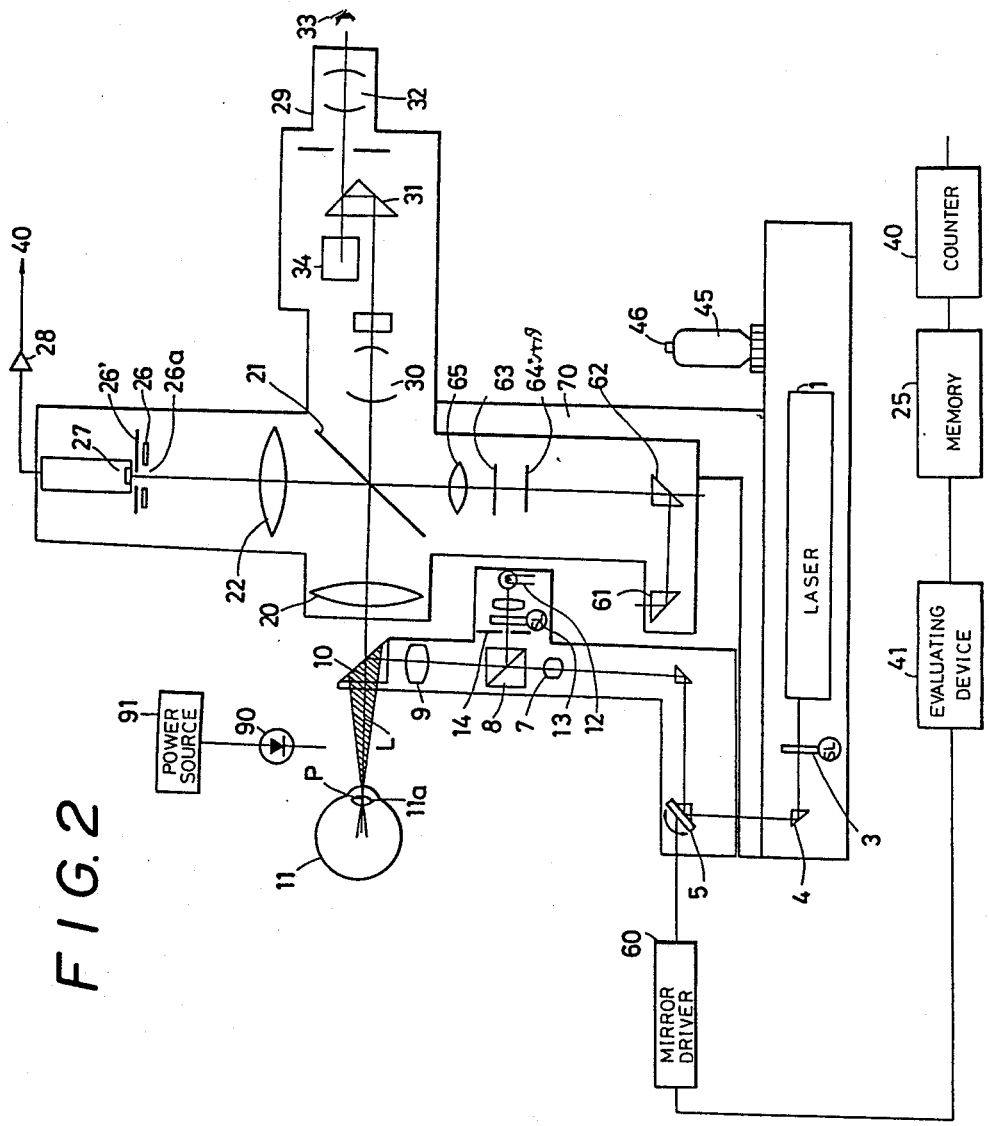
FIG. 2 is a view showing the arrangement of the optical systems of the apparatus.

FIG. 1 and FIG. 2 show the general arrangement of an ophthalmic disease detection apparatus according to the present invention. In the drawings, reference numeral 1 indicates a helium-neon or argon type laser light source. The laser light source 1 is provided on a base 2. The light emitted from the laser light source 1 is passed through a laser filter 3, a prism 4, a swingable mirror 5, a prism 6, a lens 7, a beam splitter 8, a lens 9 and a prism 10, and converged at one spot in a camera oculi 11a of a patient's eye 11.

A slit light source 12 is provided in the laser emitting portion, and the light emitted from, this slit light source 12 passes through a slit light shutter 13, a slit 14, and via the beam splitter 8, the lens 9 and the prism 10, whereupon it is imaged as a slit image on the camera oculi 11a or anterior chamber. Because the light emitted from the above mentioned laser light source 1 is converged as a spot of light, the slit light image is intended to illuminate the periphery of the light spot and thereby make the verification of the location of the spot image easy.

Adjustment as well as switching of the length of the slit along the lengthwise dimension of the slit 14 are carried out by means of an adjusting knob 15 and a switching knob 16, respectively.

Part of the laser light scattered from the spot being measured in the camera oculi 11a passes through an objective lens 20 of a detector 29, and is then divided by a beam splitter 21, whereupon a portion of the light passes through a lens 22, a prism 23, an optical fiber 24, a lens 25, and a shutter 26', and strikes a photomultiplier 27 which performs the function of a photoelectric converter. A mask 26 with a slits 26a having a certain width is disposed in the front of the photomultiplier 27, to limit the impinging of the scattered light thereon. Another portion of the scattered light divided by the beam splitter 21 is directed in another direction and passes through a variator lens 30, a prism 31, and a monitoring plate 34. The image may be observed by an examiner 33 through an eyepiece 32.

The output signal of the photomultiplier 27 is amplified by an amplifier 28 and then applied to a counter 40 for counting the number of photons, thus determining the intensity of the scattered light detected by the photomultiplier 27. The counter 40 counts the number of pulses appearing. When the photomultiplier 27 receives the scattered light greater in intensity than a predetermined value, the counter 40 produces an output signal, which is then applied to an evaluating device 41 to calculate the protein concentration in the camera oculi 11a.

The swingable mirror 5 is pivoted by a mirror driver 60 connected to the evaluating device 41 whereupon the laser beam is thereby scanned, moving the spot of laser light in the anterior chamber. As shown in FIGS. 3(A) and 3(B), the scanning of the laser beam takes place over a region S1 which is below a plane S which is perpendicular to the scanning direction T and includes the vertex 50a of the cornea 50. The plane S is selected so as not to coincide with a plane L (shown in FIG. 2 and FIG. 3(A)) that includes the optical axes of the laser beam projector and the light receiving means. The detector 29 houses an optical system for the positional alignment of the patient's eye 11 with the detection apparatus by receiving the corneal reflected light 51. The corneal reflected light 51 is received via a prism 61, passes through a prism 62, a shutter 64, a mask 63 and a lens 65, and is deflected by the beam splitter 21 toward the examiner 33. The prisms 61 and 62 are adjusted so as to receive the corneal reflected light with good efficiency. The shutter 64 is linked to the shutter 26' disposed in front of a photomultiplier 27, the arrangement being such that when the shutter 26' is open the shutter 64 is closed.

The detector 29 is affixed to a support 70. The support 70 and the laser beam projector are provided so as to be rotatable, with respect to each other, about a spindle 71, so as to allow the angle between the optical axes of the laser beam projector and the light receiving means to be adjusted to the required setting. In the preferred embodiment, detection is carried out with this angle set at about 90 degrees.

In accordance with this invention, an eye fixation light 90 constituted of a light-emitting diode or the like powered by electricity supplied from a power source 91 is disposed at a position that permits fixation of the patient's eye. The light selected for the eye fixation light 90 is of a different color than the light of the laser light source 1. For example, when the light from the laser light source is red, a green light is selected. The eye fixation light 90 can be turned in the direction indicated by the arrow by means of a link mechanism 92 to enable it to be adjusted so that it is always in an optimum position with respect to the patient's eye.

Provided on the base 2 is an input means, such as a joystick 45 equipped with a push-button 46, and this can be operated to insert the laser filter 3, the slit light shutter 13, the shutter 26' and the shutter 64 into, or retract the elements from, the respective optical system.

The operation of the detection apparatus arranged thus will now be described. In conducting the detection, the slit light source 12 is activated and an image of the slit 14 is formed, via the beam splitter 8, the lens 9 and the prism 10, on a part that includes the measuring point P of the anterior chamber 11a. Following this, light from the laser light source 1 is converged on the measuring point P via the optical system.

A portion of the light from the measuring point P is simultaneously directed by the beam splitter 21 to the examiner 33 for observation and through the lens 22, a prism 23 and the mask 26 to impinge on the photomultiplier 27.

The swingable mirror 5 is pivoted by the mirror driver 60 in the direction indicated by the arrow, to scan the laser beam in the direction T across a scanning width S1 which is below the plane S which includes the corneal vertex, as illustrated in FIG. 3(B).

The photomultiplier 27 receives, via the slit 26a, the incident scattered laser light, detects the intensity of the light that has been diffused by protein particles in the anterior chamber 11a and converts this into a corresponding pulse train which is counted by a counter 40 as number of pulses per unit time and the count values are stored in a memory 25 allocated for each unit time. The evaluating device 41 calculates the data contained in the memory 25 to evaluate the concentration of protein in the anterior chamber.

In this embodiment harmful light rays can be cut, because as the cornea 50 is convex, the corneal reflected light 51 is directed away from plane L which includes the optical axis of the light receiving means, and therefore does not impinge on the photomultiplier 27. The scanning region is not limited to the region S1 but may be other regions S2 to S4 (FIG. 3(B)) that do not include the plane S. Although region S2 has the drawback that the eyelid forms an obstruction, the same effect may be obtained by keeping the eye open by artificial means. In the cases of regions S3 and S4, because the optical axis of the light receiving means is required to intersect the scanning direction at a right angle, coordination is difficult because the examiner has to look down (or look up) at a slight lateral angle but the same effect can still be attained that is attained with S1. However, taking into consideration the utilization of the corneal reflected light for the purpose of positional alignment, the S1 region is the most preferable selection.

The extremely low intensity of the scattered laser light makes it susceptible to light other than light from the detection target, which manifests itself as noise. Taking the detection of the anterior chamber as an example, if the detection area is too close to the crystalline lens, light scattering from the crystalline lens is picked up as noise that influences the detection results. Also, because the cornea has a strong lens effect, light other than light impinging from the normal line is refracted by the cornea surface. Hence, when the area on which the light impinges is changed the degree of refraction also changes, disturbing the relationship between the detection area (laser light converging area) and the light receiving means (mask). For this reason, accurate positional alignment is necessary in order to receive the light scattered from the target object (the patient's eye).

Because of this, this embodiment of the invention incorporates an optical alignment system (elements 61 to 65). With this system, the surface that receives the corneal reflected light 51 is fixed to the laser beam projector or the light receiving means. In the embodiment illustrated in FIG. 2, the prism 61 forms the light receiving surface. During the positional alignment process, the shutter 64 is opened and the shutter 26' is closed. Each of the optical systems is disposed so that when, in this state, the patient's eye 11 is correctly aligned with the detection apparatus, the examiner 33 can observe the corneal reflected light within his field of vision.

In this case, as illustrated in FIG. 4, it is preferable to use an arrangement wherein a condenser lens 66 is disposed in front of the shutter 64 and, using a stop 63' that has a transmitting portion or a diffusing surface 63'a, the corneal reflected light 51 is converged on the transmitting portion 63'a. An advantage of this embodiment is that the observed corneal reflected light image is brighter, and as the brightness is related to operating distance, the operating distance can be monitored approximately.

With reference to FIG. 2, the prisms 61 and 62 may be coupled by a light guide and, furthermore, a diffusing plate may be employed in place of the prism 62. Again, because the laser beam projector and the light receiving means are in a predetermined positional relationship (the optical axes thereof set at 90 degrees, for example, as described later), the surface that receives the corneal reflected light may be fixed to the laser beam projector.

With respect to the positional alignment, as illustrated in FIGS. 5(A) and 5(B), a light receiving plate 72 constituted of ground glass or the like and having a scale with graduations may be used that will enable the examiner to make a direct visual observation. As indicated by the dashed line, the size and position of a corneal reflected light image 72a as observed by the light receiving plate 72 depends on the positional relationship of the patient's eye 11 and the detection apparatus, which makes it possible to carry out the positional alignment by a simple method. Also, as shown in FIGS. 5(C) and 5(D), it is possible to dispose a plurality of photodiodes on the light receiving plate 72 for positional alignment purposes. In the example illustrated by FIG. 5(C) the detection apparatus is in alignment when no light is received by the four photodiodes 73a and light is received by the four photodiodes 73b. In the example shown in FIG. 5(D) alignment has been achieved when light is not received by a photodiode 74a and light is received by the four-part photodiode 74b and photodiode 74c.

Each of the embodiments illustrated in FIG. 5 enables three-dimensional positional alignment to be carried out using a simple arrangement and eliminates the need for registration light sources, targets and other such parts relating to laser beam projector systems for positional alignment. Also, when photodiodes are employed, it is possible to have the photodiodes indicate the positional alignment in accordance with the received light state.

With the radius of curvature of the cornea being around 6 mm to 8 mm, and the depth of the aqueous humor in the anterior chamber being on the order of 3 mm, the rays that are brought to convergence on the aqueous humor of the anterior chamber are, after reflection at the cornea, once converged and then diffused. Utilizing this converged light spot for positional alignment is convenient for obtaining positional alignment information because the spot has a high luminance, but as in the case of some detection areas in the aqueous humor the light might be converged quite close to the cornea, for the light receiving surface it is preferable to choose a place where the light has become diffused.

Also in accordance with this embodiment, as illustrated in FIG. 6 the light receiving means and the laser beam projector are disposed so that their optical axes cross at around 90 degrees. At this time an image 26" is formed at the beam waist 80' on the optical axis of the light receiving means at a position which is a conjugate with that of the mask.

Figure 7:
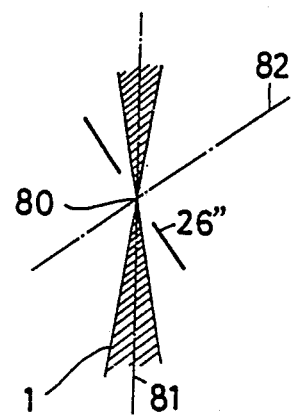
FIG. 7 is a view showing the positional arrangement when the optical axes deviate from the 90-degree relationship.

When the optical axis 81 of the laser beam projector and the optical axis 82 of the light receiving means are disposed so that they deviate from the aforesaid 90 degrees, as illustrated in FIG. 7, diffused laser beam light will move further out of focus as it approaches the edge of the mask, so that when overscanning (i.e., scanning that exceeds the aperture of the mask 26a) is used, the received light signal will become indistinct.

Figure 8A:
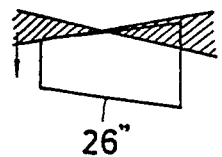
FIG. 8(A) and 8(B) are explanatory views of the scanning state when the optical axes deviate from the 90-degree relationship.
Figure 8B:
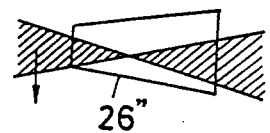

When there is a deviation from the 90-degree relationship, it is possible to circumvent the above problem by an arrangement based on the shine-proof principle, but the image 26" of the rectangular mask 26 becomes trapezoidal in shape, as shown in FIG. 8(A) and 8(B). In such a case, when scanning is performed from FIG. 8(A) to FIG. 8(B), for example, the rise of the signal waveform is blunted, so that the shape of the mask 26 is made into a reverse trapezoid so that the image 26" thereof forms a rectangle at the position of the laser beam projector beam waist.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An apparatus for detecting ophthalmic diseases in a patient's eye comprising:
    a laser source for producing a laser beam;
    a laser beam projector for projecting said laser beam;
    means for focusing said laser beam at a selected spot in said patient's eye;
    means for deflecting said laser beam in a predetermined direction to scan an area including said selected spot in the patient's eye;
    photoelectric converting means for receiving light scattered from said patient's eye and photoelectrically converting it into an electrical signal for use in detecting ophthalmic diseases in the patient's eye; and
    a mask disposed in the front of said photoelectric converting means and formed thereon with a slit having a predetermined width to limit the impinging of the scattered light on said photoelectric converting means;
    wherein said laser beam is so deflected that it scans an area in the patient's eye except for a plane which is perpendicular to the scanning direction and includes the corneal vertex of the patient's eye.

2. An apparatus as set forth in claim 1, wherein said area to be scanned lies under the plane which is perpendicular to the scanning direction and includes the corneal vertex of the patient's eye.

3. An apparatus as set forth in claim 1, wherein at least one of the size and position of corneal reflex light on a surface fixed to one of said laser beam projector and said light receiving means is determined for positional alignment between the patient's eye and the apparatus.

4. An apparatus as set forth in claim 1, wherein said laser beam projector and light receiving means are arranged so that their optical axes cross substantially at right angles with each other.

5. An apparatus as set forth in claim 1, wherein said laser beam projector and light receiving means are arranged so that their optical axes cross at an angle other than 90 degrees.

6. An apparatus as set forth in claim 5, wherein said mask is trapezoidal.

* * * * *